United States Patent
Jung et al.

(10) Patent No.: US 8,636,033 B2
(45) Date of Patent: Jan. 28, 2014

(54) MICROFLUIDIC DEVICE INITIALIZATION METHOD, MICROFLUIDIC DEVICE INITIALIZATION APPARATUS AND MICROFLUIDIC DEVICE PACKAGE

(75) Inventors: Won-jong Jung, Seongnam-si (KR); Jae-young Kim, Seoul (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 585 days.

(21) Appl. No.: 12/757,374

(22) Filed: Apr. 9, 2010

(65) Prior Publication Data
US 2011/0094591 A1    Apr. 28, 2011

(30) Foreign Application Priority Data

Oct. 28, 2009    (KR) ................. 10-2009-0102821

(51) Int. Cl.
*F15C 1/06* (2006.01)

(52) U.S. Cl.
USPC ............ 137/833; 137/829; 137/907; 436/180

(58) Field of Classification Search
USPC ................. 137/814, 822, 829, 832, 833, 907; 422/102, 103, 104, 400; 436/52, 148, 436/180
See application file for complete search history.

(56) References Cited

U.S. PATENT DOCUMENTS

| | | | |
|---|---|---|---|
| 6,321,791 B1 * | 11/2001 | Chow | 137/833 |
| 6,814,859 B2 | 11/2004 | Koehler et al. | |
| 7,069,952 B1 * | 7/2006 | McReynolds et al. | 137/833 |
| 7,445,926 B2 * | 11/2008 | Mathies et al. | 435/288.5 |
| 7,708,950 B2 * | 5/2010 | Yamada et al. | 422/504 |
| 7,850,930 B2 * | 12/2010 | Miyamoto et al. | 422/224 |
| 8,286,665 B2 * | 10/2012 | Mathies et al. | 137/832 |
| 2004/0092033 A1 * | 5/2004 | Gustafson et al. | 436/180 |
| 2004/0109793 A1 * | 6/2004 | McNeely et al. | 422/100 |
| 2004/0258572 A1 * | 12/2004 | Haibara et al. | 422/100 |
| 2005/0201901 A1 * | 9/2005 | Grossman et al. | 422/100 |
| 2005/0255003 A1 * | 11/2005 | Summersgill et al. | 422/100 |
| 2005/0266582 A1 | 12/2005 | Modlin et al. | |
| 2006/0013731 A1 | 1/2006 | Stout et al. | |
| 2006/0078475 A1 * | 4/2006 | Tai et al. | 422/102 |
| 2006/0211134 A1 * | 9/2006 | Kennedy et al. | 436/180 |
| 2007/0003434 A1 * | 1/2007 | Padmanabhan et al. | 422/57 |
| 2007/0237686 A1 | 10/2007 | Mathies et al. | |
| 2007/0278100 A1 | 12/2007 | Qian et al. | |
| 2008/0035875 A1 | 2/2008 | Tai et al. | |

FOREIGN PATENT DOCUMENTS

| | | |
|---|---|---|
| JP | 2004-211898 A | 7/2004 |
| KR | 1020070052958 A | 5/2007 |
| KR | 1020090004954 A | 1/2009 |

* cited by examiner

*Primary Examiner* — Eric Keasel
*Assistant Examiner* — R. K. Arundale
(74) *Attorney, Agent, or Firm* — Leydig, Voit & Mayer, Ltd.

(57) ABSTRACT

In a method for initialization of a microfluidic device including a first substrate including a microfluidic channel disposed therein, a valve seat disposed in a microfluidic channel and protruding from the first substrate, and a second substrate disposed opposite to the first substrate and including a space formed therein and corresponding to the valve seat, and a polymer film disposed between the first and second substrates, the method includes separating the polymer film from a surface of the valve seat by applying a positive pressure into the microfluidic channel of the first substrate and applying a negative pressure into the space of the second substrate.

12 Claims, 4 Drawing Sheets

FIG. 7 ated by this app are to the upper substrate and through which a sample is supplied.

MICROFLUIDIC DEVICE INITIALIZATION METHOD, MICROFLUIDIC DEVICE INITIALIZATION APPARATUS AND MICROFLUIDIC DEVICE PACKAGE

CROSS-REFERENCE TO RELATED APPLICATION

This application claims priority to Korean Patent Application No. 10-2009-0102821, filed on Oct. 28, 2009, and all the benefits accruing therefrom under 35 U.S.C. §119, the content of which in its entirety is herein incorporated by reference.

BACKGROUND

1) Field

The general inventive concept relates to microfluidic device initialization methods, microfluidic device initialization apparatuses and microfluidic device packages, and more particularly, to methods and apparatuses for initializing on and off states of a valve using a polymer film in a microfluidic device, and microfluidic device packages in which on and off states of a valve are easily and efficiently initialized.

2) Description of the Related Art

A clinical or environment-related sample is generally analyzed by performing a series of biochemical, chemical and/or mechanical processes. Recently, technologies for diagnosing or monitoring a biological sample have been developed. Due to high accuracy and sensitivity requirements, a molecular diagnosis method based on a nucleic acid is increasingly and broadly being used to diagnose infectious diseases and cancers to study pharmacogenomics, as well as to develop new medicines.

Microfluidic devices are sometimes used to analyze a sample in a simple and precise manner. The microfluidic device typically includes a thin substrate in which sample inlets, sample outlets, microfluidic channels and reaction chambers are formed, and thus various tests may be simply performed on one sample. In the microfluidic device, valves may be included in the microfluidic channels to provide a sample and a reagent at predetermined locations in the microfluidic device. The valves are generally formed using a thin polymer film. However, when a microfluidic device includes the valves formed using the thin polymer film, on and off states of the valves needs to be precisely and accurately controlled.

SUMMARY

The general inventive concept includes methods and apparatuses for initializing on and off states of a valve using a polymer film in a microfluidic device.

The general inventive also concept includes microfluidic device packages in which on and off states of a valve are easily initialized.

Provided is a method for initialization of a microfluidic device including a first substrate including a microfluidic channel disposed therein, a valve seat disposed in a microfluidic channel and protruding from the first substrate, a second substrate including a space formed therein and corresponding to the valve seat, and a polymer film disposed between the first and second substrates. The method includes separating the polymer film from a surface of the valve seat by supplying a positive pressure to the microfluidic channel of the first substrate and supplying a negative pressure to the space of the second substrate.

The method may further include pushing the polymer film toward the valve seat by supplying the positive pressure to the space of the second substrate.

The separating the polymer film from the surface of the valve seat and the pushing the polymer film toward the valve seat may be performed at least twice.

The separating the polymer film from the surface of the valve seat may include increasing a magnitude of at least one of the positive pressure and the negative pressure until the polymer film is separated from the surface of the valve seat.

The separating the polymer film from the surface of the valve seat may be performed after the microfluidic device is manufactured and/or immediately before the microfluidic device is used.

Also provided is a microfluidic device initialization apparatus that includes a lower substrate, an upper substrate disposed opposite to the lower substrate, a lower fixing unit formed in an inner surface of the lower substrate, an upper fixing unit formed in an inner surface of the upper substrate, and air pressure ports disposed on outer surfaces of the lower and upper substrates and through which at least one of a negative pressure and a positive pressure is supplied from an external device. The lower substrate and the upper substrate are combined with each other at opposite sides of a microfluidic device to initialize the microfluidic device, the microfluidic device is disposed in a space defined by the lower and upper fixing units when the lower substrate and the upper substrate are combined with each other, and at least one of the negative pressure and the positive pressure is supplied to the microfluidic device through the air pressure holes.

The microfluidic device initialization apparatus may further include combination grooves formed in the inner surface of the lower substrate; and combination poles disposed on the inner surface of the upper substrate where the combination poles are inserted into the combination grooves when the lower substrate and the upper substrate are combined with each other.

The air pressure holes formed in the lower fixing unit of the lower substrate may be connected to holes formed in a first substrate of the microfluidic device when the microfluidic device is disposed between the combined upper and lower substrates.

The air pressure holes formed in the upper fixing unit of the upper substrate may be connected to holes formed in a second substrate of the microfluidic device when the microfluidic device is disposed between the combined upper and lower substrates.

The air pressure holes formed in the lower and upper fixing units may be connected to air inlet holes of the microfluidic device when the microfluidic device is disposed between the combined upper and lower substrates.

The air pressure ports may include a first air pressure port disposed on the lower substrate; and second and third air pressure ports disposed on the upper substrate.

The first and second air pressure ports may receive a positive pressure and the third air pressure port may receive a negative pressure.

Each of the first through third air pressure ports may be one of an air pressure port through which at least one of a negative pressure and a positive pressure is applied and a sample inlet port through which a sample is supplied.

The microfluidic device initialization apparatus may further include at least one sample inlet port disposed on the lower substrate and through which a sample is supplied.

According the microfluidic device initialization apparatus may further include at least one sample inlet port disposed on the upper substrate and through which a sample is supplied.

The microfluidic device initialization apparatus may further include a sample analysis system which analyzes a sample using the microfluidic device.

Also provided is a microfluidic device package that includes a microfluidic device and a microfluidic device initialization apparatus. The microfluidic device includes a first substrate, a microfluidic channel disposed in the first substrate, a valve seat disposed in the microfluidic channel and protruding from the first substrate, a first hole formed in the first substrate and connected to the microfluidic channel, a second substrate disposed opposite to the first substrate, a space formed in the second substrate and corresponding to the valve seat, a second hole formed in the second substrate and connected to the space, and a polymer film disposed between the first and second substrates. The microfluidic device initialization apparatus includes a lower substrate, an upper substrate disposed opposite to the lower substrate, a lower fixing unit formed in an inner surface of the lower substrate, an upper fixing unit formed in an inner surface of the upper substrate, air pressure holes formed in each of the inner surface of the lower fixing unit in the lower substrate and the inner surface of the upper fixing unit in the upper substrate, and air pressure ports disposed on outer surfaces of the lower and upper substrates and through which at least one of a negative pressure and a positive pressure is supplied from an external device. The lower substrate and the upper substrate of the microfluidic device initialization apparatus are combined with each other at opposite sides of the microfluidic device, the microfluidic device is disposed in a space defined by the lower and upper fixing units, and is integrated between the lower and the upper substrates of the microfluidic device initialization apparatus, and at least one of the negative pressure and the positive pressure is supplied to the microfluidic device through at least one of the air pressure holes, the first hole and the second hole.

Further provided is a microfluidic device initialization apparatus that includes a first substrate, a first plurality of needles disposed on a lower surface of the first substrate, and at least one first air pressure port disposed on at least one of an upper surface and a side surface of the first substrate and through which at least one of a negative pressure and a positive pressure is supplied from an external device, where at least one of the negative pressure and a positive pressure is supplied to a microfluidic device through the first plurality of needles.

The first plurality of needles is disposed in an array, and locations of needles of the first plurality of needles correspond to holes formed in a first surface of the microfluidic device.

The locations of the needles correspond only to holes related to opening and closing operations of valves of the microfluidic device.

The microfluidic device initialization apparatus may further include a second substrate, a second plurality of needles disposed on a lower surface of the second substrate, and at least one second air pressure port disposed on at least one of an upper surface and a side surface of the second substrate and through which at least one of a negative pressure and a positive pressure is supplied from the external device, where at least one of the negative pressure and a positive pressure is supplied to the microfluidic device through the second plurality of needles, the second plurality of needles is disposed in an array, and locations of needles of the second plurality of needles correspond to holes formed in a second surface of the microfluidic device.

Also provided is a microfluidic device that includes a first substrate, a microfluidic channel disposed in the first substrate, a valve seat disposed in the microfluidic channel and protruding from the first substrate, a first hole formed in the first substrate and connected to the microfluidic channel, a second substrate disposed opposite to the first substrate, a space formed in the second substrate and corresponding to the valve seat; a second hole formed in the second substrate and connected to the space, and a polymer film disposed between the first and second substrates, where the polymer film is configured to be separated from a surface of the valve seat when a positive pressure into the microfluidic channel of the first substrate is applied through the first hole and a negative pressure into the space of the second substrate is applied through the second hole.

BRIEF DESCRIPTION OF THE DRAWINGS

The above and/or other aspects of this disclosure will become more apparent by describing in further detail embodiments thereof with reference to the accompanying drawings, in which.

DETAILED DESCRIPTION

The general inventive concept now will be described more fully hereinafter with reference to the accompanying drawings, in which various example embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

One or more embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the present claims.

Figure 1:
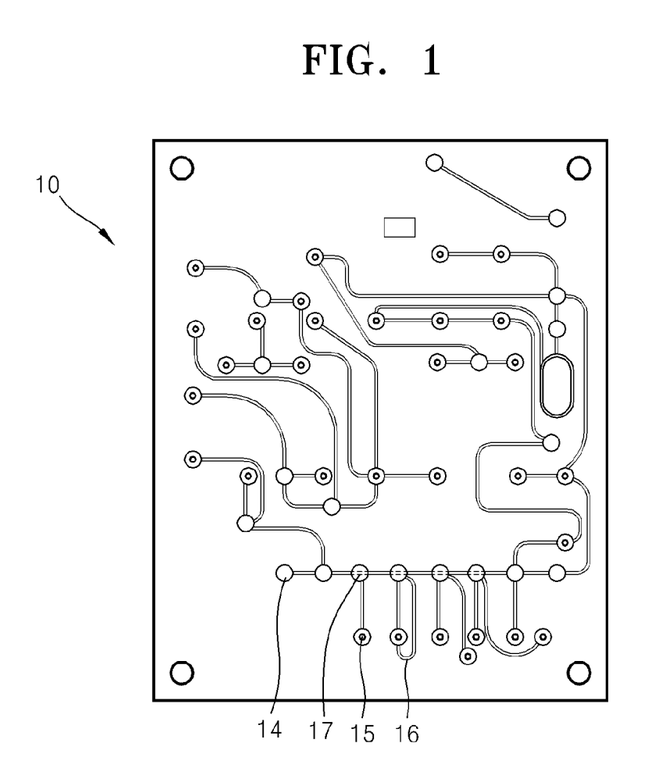
FIG. 1 is a plan view of an embodiment of a microfluidic device.

FIG. 1 is a plan view of an embodiment of a microfluidic device 10.

As shown in FIG. 1, the microfluidic device 10 includes holes 15 through which a sample or air enters and/or exits, reaction chambers 14 in which a chemical/biological reaction of the sample occurs, microfluidic channels 16 through which the sample flows, and valves 17 which control a flow of the sample at a determined position on a thin and transparent substrate. In an embodiment, the holes 15 may be a sample inlet hole for a sample to enter or exit, and/or an air pressure inlet hole for air that controls the valves 17 to enter or exit. The valves 17 are disposed in the microfluidic channels 16, and control the flow of the sample in the microfluidic channels by allowing or blocking passage of the sample in the microfluidic channels 16.

The valves 17 may be formed using a thin polymer film.

Figure 2:
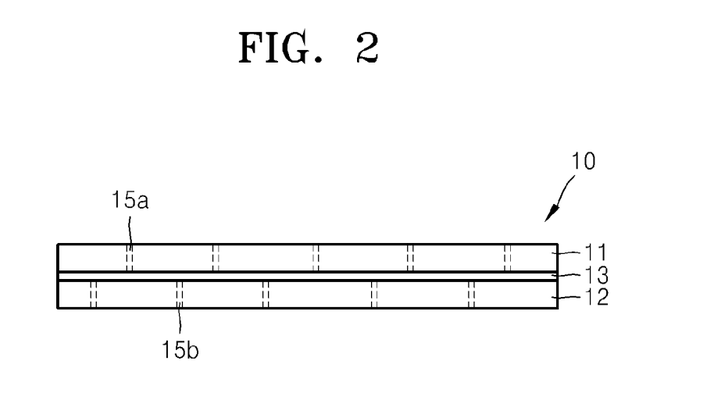
FIG. 2 is a cross-sectional view of the microfluidic device shown in FIG. 1.

FIG. 2 is a cross-sectional view of the microfluidic device 10 of FIG. 1. As shown in FIG. 2, the valves 17 are disposed in the microfluidic channels 16 of the microfluidic device 10.

Referring to FIGS. 1 and 2, the microfluidic device 10 may include a first substrate 11, which may be transparent, and a second substrate 12, which may be transparent, and a polymer film 13 disposed between the first and second substrates 11 and 12. As shown in FIG. 2, a first hole 15a and a second hole 15b are formed in the first and second substrate 11 and 12, respectively. Although not illustrated in FIG. 2, the microfluidic channels 16 may be formed in each of the first and second substrates 11 and 12.

Figure 3:
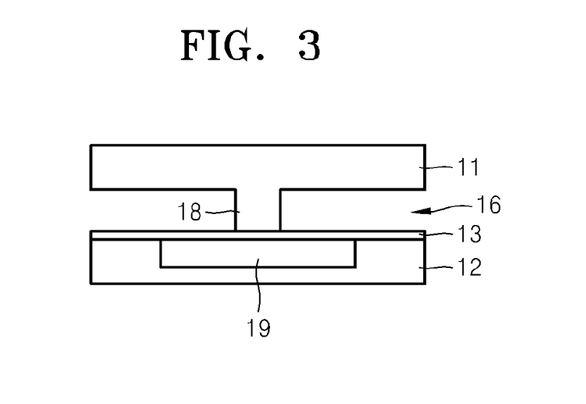
FIG. 3 is a cross-sectional view of a valve of the microfluidic device shown in FIG. 1.

FIG. 3 is a cross-sectional view of the valve 17 disposed in a microfluidic channel 16 of the microfluidic device 10 in FIG. 1.

Referring to FIGS. 1 through 3, a valve seat 18 is disposed protruding from the first substrate 11 in the microfluidic channel 16 formed in the first substrate 11. In an embodiment, a space 19, which may be an empty space 19, is formed in the second substrate 12 at a location corresponding to the valve seat 18. In an embodiment, the space 19 may be formed by etching the second substrate 12, but additional embodiments are not limited thereto. The space 19 and the valve seat 18 are disposed with a predetermined distance therebetween, and the polymer film 13 is disposed between the first and second substrates 11 and 12 and contacting the space 19 and the valve seat 18. In an embodiment, the microfluidic channel 16 may be connected to at least one hole 15 of the holes 15 through which a sample enters and/or exits, and the space 19 may be connected to at least another hole 15 of the holes 15 through which air enters and/or exits.

In an embodiment, when a negative pressure, e.g., a vacuum, is supplied to the space 19 in the valve 17, the polymer film 13 is pulled toward the space 19, and the microfluidic channel 16 is thereby opened. When the microfluidic channel 16 is opened, the sample that enters through the holes 15 flows to a predetermined location through the microfluidic channel 16. When a positive pressure (relative to the vacuum), e.g., an air pressure, is applied into the space 19 in the valve 17, the polymer film 13 is pushed toward the valve seat 18, and the microfluidic channel 16 is thereby closed. When the microfluidic channel 16 is closed, the sample stops flowing.

When the microfluidic device 10 has not been used for a certain amount of time or after the microfluidic device 10 is manufactured, the polymer film 13 naturally adheres to the surface of the valve seat 18, due to a chemical or physical reaction, for example, and the valve 17 thereby will not properly open or close during operation of the microfluidic device 10. A material having a low surface energy may be coated on the surface of the valve seat 18 to prevent adhering between the polymer film 13 and the surface of the valve seat 18. However, it is not easy to coat a material onto a predetermined region of the first substrate 11, such as the surface of the valve seat 18.

In one or more embodiments, however, after the microfluidic device 10 is manufactured and/or before the microfluidic device 10 is used, the microfluidic device 10 is initialized, and the undesirable adherence of the polymer film 13 and the surface of the valve seat 18 is thereby effectively prevented. Hereinafter, initialization of the microfluidic device 10 refers to an operation of separating the polymer film 13, which is adhered to the surface of the valve seat 18, from the surface of the valve seat 18.

Figure 4:
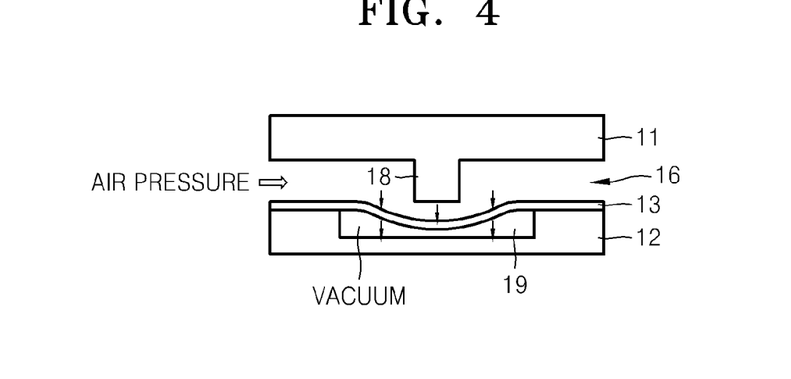
FIG. 4 is a cross-sectional view of the valve of FIG. 3 opened by an embodiment of a microfluidic device initialization method.
Figure 5:
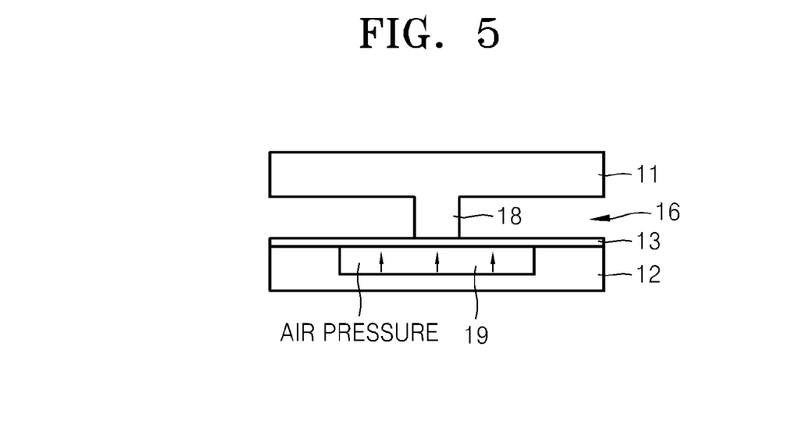
FIG. 5 is a cross-sectional view of the valve of FIG. 3 closed by the microfluidic device initialization method.

FIG. 4 is a cross-sectional view of the valve 17 of FIG. 3 opened by an example embodiment of a microfluidic device initialization method. FIG. 5 is a cross-sectional view of the valve 17 of FIG. 3 closed by the microfluidic device initialization method according to one or more embodiments.

Referring to FIGS. 1 through 4, the positive pressure, e.g., the air pressure, is supplied to the microfluidic channel 16 of the first substrate 11, and the negative pressure (relative to the air pressure), e.g., the vacuum, is supplied to the space 19 of the second substrate 12. In an embodiment, when the microfluidic device 10 is initialized, a sample is not yet supplied to the first substrate 11, and thus the positive pressure, e.g., the air pressure, is effectively supplied into the microfluidic channel 16. In an embodiment, the polymer film 13 may not be separated from the surface of the valve seat 18 by the negative pressure, e.g., by the vacuum, which is supplied to the space 19 of the second substrate 12, but may be separated from the surface of the valve seat 18 when the positive pressure, e.g., the air pressure, is supplied to the microfluidic channel 16. In an embodiment, the positive pressure, e.g., the air pressure, supplied to the microfluidic channel 16 and/or the negative pressure, e.g., the vacuum, supplied to the space 19 may be increased for a predetermined period, and the polymer film 13 is thereby effectively separated from the surface of the valve seat 18. When the microfluidic device 10 is initialized as described above, the reliability of an operation of the valve 17 in the microfluidic device 10 is substantially increased.

When the polymer film 13 is separated from the surface of the valve seat 18, as illustrated in FIG. 5, the valve 17 may be closed by supplying the positive pressure, e.g., the air pressure, to the space 19. In an embodiment, the opening operation illustrated in FIG. 4 and the closing operation illustrated in FIG. 5 may be repeated for a predetermined period of time or a predetermined number of times.

In an embodiment, the polymer film 13 may be separated from the surface of the valve seat 18 with respect to all of the valves 17 in the microfluidic device 10 at the same time to rapidly initialize the microfluidic device 10. When the polymer film 13 is separated from the surface of the valve seat 18 of all of the vales 17 at the same time, the positive pressure, e.g., the air pressure, or the negative pressure, e.g., the vacuum, is supplied into all of the holes 15 corresponding to the valves 17 at the same time. In an embodiment, a microfluidic device initialization apparatus may be connected to all of the holes 15 corresponding to the valves 17 in the microfluidic device 10 to apply the positive pressure, e.g., the air pressure, or the negative pressure, e.g., the vacuum, into the holes 15 at the same time, and the microfluidic device 10 is thereby rapidly initialized.

Figure 6A:
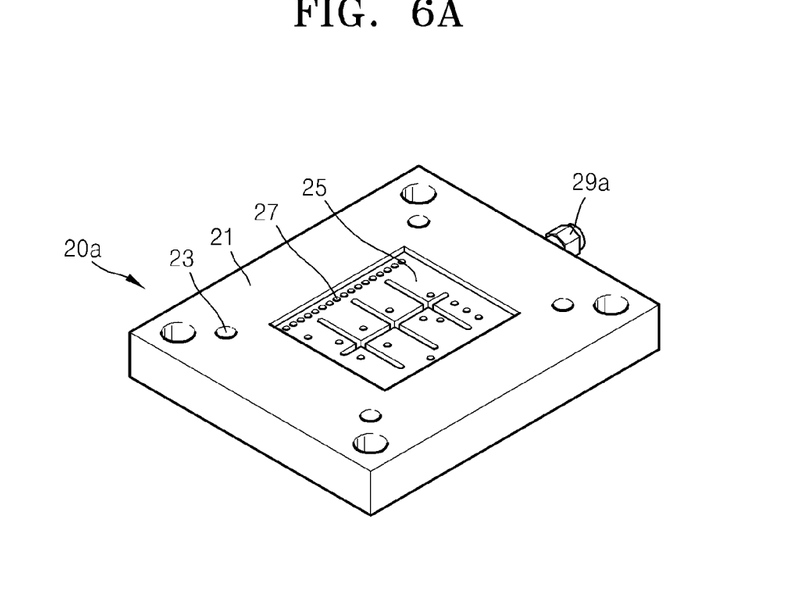
FIGS. 6A and 6B are perspective views of an embodiment of a microfluidic device initialization apparatus that initializes the microfluidic device shown in FIG. 1.
Figure 6B:
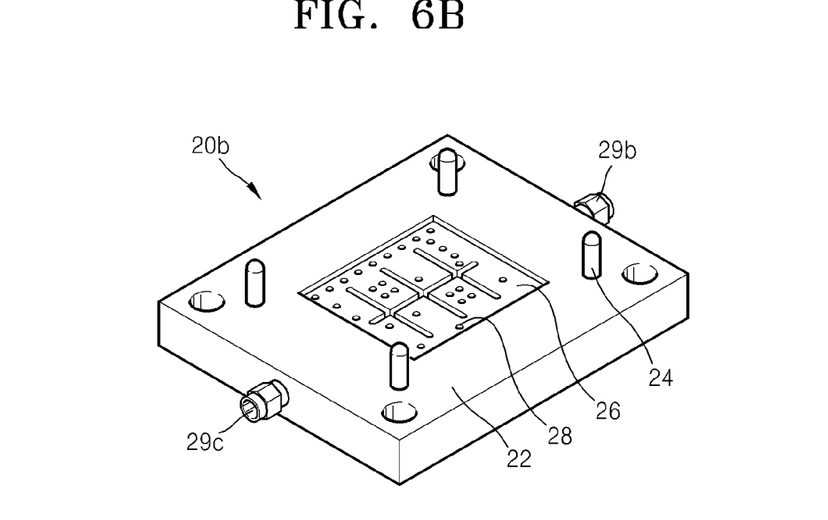

FIGS. 6A and 6B are perspective views of an embodiment of a microfluidic device initialization apparatus that initializes the microfluidic device 10 of FIG. 1. More particularly, FIG. 6A is a perspective view of an embodiment of a lower jig 20a of the microfluidic device initialization apparatus and FIG. 6B is a perspective view of an embodiment of an upper jig 20b of the microfluidic device initialization apparatus. FIGS. 6A and 6B will now be described referring also to FIGS. 1 through 3.

As shown in FIGS. 6A and 6B, the microfluidic device initialization apparatus includes the lower jig 20a and the upper jig 20b, which may be disposed at opposite sides of the microfluidic device 10, to be combined with each other. In an embodiment, a the lower jig 20a and the upper jig 20b include a lower substrate 21 and an upper substrate 22, respectively, and lower fixing unit 25 and an upper fixing unit 26 are formed in center portions of inner surfaces of the lower and upper substrates 21 and 22, respectively, and the microfluidic device 10 is thereby disposed in a space defined by the lower and upper fixing units 25 and 26 when the lower jig 20a and the upper jig 20b are combined. In an embodiment, combination grooves 23 are formed in the inner surface of the lower substrate 21 outside the upper fixing unit 25, e.g., a peripheral portion of the inner surface of the lower substrate 21 surrounding the center portion thereof, and combination poles 24 are disposed on the inner surface of the upper substrate 22 outside the lower fixing unit 26, e.g., a peripheral portion of the inner surface of the upper substrate 22 surrounding the center portion thereof. When the lower and upper jigs 20a and 20b disposed at the opposite sides of the microfluidic device 10, respectively, are firmly combined by inserting the combination poles 24 of the upper substrate 22 into the combination grooves 23 of the lower substrate 21, the microfluidic device 10 may be disposed in a space defined by the lower and upper fixing units 25 and 26.

In an embodiment, air pressure holes 27 and 28, through which a positive pressure, e.g., an air pressure, or a negative pressure (relative to the positive pressure), e.g., a vacuum, is supplied to the valves of the microfluidic device 10, are formed in the lower and upper fixing units 25 and 26, respectively. In an embodiment, the air pressure holes 27 formed in the lower fixing unit 25 of the lower substrate 21 may be formed corresponding to the holes 15 formed in the first substrate 11 of the microfluidic device 10 disposed in the space defined by the lower and upper fixing units 25 and 26 when the lower jig 20a and the upper jig 20b are combined. In an embodiment, the air pressure holes 28 formed in the upper fixing unit 26 of the upper substrate 22 may correspond to the holes 15 formed in the second substrate 12 of the microfluidic device 10 disposed in the space defined by the lower and upper fixing units 25 and 26 when the lower jig 20a and the upper jig 20b are combined. In another embodiment, the air pressure holes 27 and 28 do not need to correspond to all of the holes 15 of the microfluidic device 10, and may be formed to correspond to only the holes 15 related to opening and closing operations of the valves 17 according to a predetermined design.

A first air pressure port 29a and second and third air pressure ports 29b and 29c, which may be connected to a vacuum pump or an air pressure pump to apply the negative pressure, e.g., the vacuum, or the positive pressure, e.g., the air pressure, to the microfluidic device 10 through the air pressure holes 27 and 28, are disposed on side surfaces of the lower and upper substrates 21 and 22, respectively. In an embodiment, the first air pressure port 29a of the lower jig 20a may be connected to a first air pressure pump, the second air pressure port 29b of the upper jig 20b may be connected to a second air pressure pump, and the third air pressure port 29c of the upper jig 22 may be connected to a vacuum pump. When the valves 17 are opened as illustrated in FIG. 4 to initialize the microfluidic device 10, the positive pressure, e.g., the air pressure, may be supplied to the microfluidic channels 16 of the first substrate 11 through the first air pressure port 29a, and the negative pressure, e.g., the vacuum, are supplied to the space 19 of the second substrate 12 through the third air pressure port 29c. When the valves 17 are closed, as illustrated in FIG. 5, to initialize the microfluidic device 10, the positive pressure, e.g., the air pressure, is supplied to the space 19 of the second substrate 12 through the second air pressure port 29b. In an embodiment, the first through third air pressure ports 29a, 29b and 29c are disposed on side surfaces of the lower and upper substrates 21 and 22, but additional embodiments are not limited thereto. In another embodiment, for example, the first through third air pressure ports 29a, 29b and 29c may be disposed on the other surfaces of the lower and upper substrates 21 and 22 according to a predetermined design, e.g., the first through third air pressure ports 29a, 29b and 29c may be disposed on front or outer surfaces of the lower and upper substrates 21 and 22.

As described herein, the microfluidic device initialization apparatus may include jigs, and the microfluidic device initialization apparatus may be separated from the microfluidic device 10. In an embodiment, the microfluidic device initialization apparatus may be separated from an analysis system for analyzing and observing a sample by using the microfluidic device 10, and the microfluidic device 10 may be initialized by using the microfluidic device initialization apparatus after the microfluidic device 10 is manufactured such that the initialized microfluidic device 10 may be provided to a user, or the microfluidic device 10 may be initialized by using the microfluidic device initialization apparatus before an end user uses the microfluidic device 10 such that a sample may be analyzed by setting the initialized microfluidic device 10 in a sample analysis system.

In another embodiment, the microfluidic device initialization apparatus may be integrated with the microfluidic device 10 or a sample analysis system of the microfluidic device 10 to be initialized.

In an embodiment, a microfluidic device package may be manufactured by using the microfluidic device initialization apparatus. More particularly, the microfluidic device 10 may be disposed between the lower and upper jigs 20a and 20b of the microfluidic device initialization apparatus, and the microfluidic device 10 and the microfluidic device initialization apparatus may be combined as one package product. When the microfluidic device 10 is integrated with the microfluidic device initialization apparatus as a microfluidic device package, a user may initialize the microfluidic device 10 without using an additional initialization apparatus, and a manufacturer may initialize a manufactured microfluidic device 10 without transferring the manufactured microfluidic device 10 to an initialization apparatus.

When the microfluidic device 10 and the microfluidic device initialization apparatus are integrated into a package, the first air pressure port 29a of the lower jig 20a may be an inlet port of a microfluidic sample as well as an air pressure. The holes 15 formed in the first substrate 11 may be an air inlet hole, through which a positive pressure, e.g., an air pressure, is applied when the microfluidic device 10 is initialized, and a sample inlet hole, through which a microfluidic sample is supplied when the microfluidic sample is analyzed. Accordingly, when the microfluidic device 10 is used to analyze a sample after being initialized, the sample may be supplied to the microfluidic device 10 through the first air pressure port 29a. In another embodiment, an additional sample inlet port, e.g., at least one port (not shown) through which a sample may be supplied, may be disposed on the lower substrate 21. In an embodiment, in addition to the second and third air pressure ports 29b and 29c, at least one port (not shown) may be disposed on the upper substrate 22 in FIG. 6B. In an embodiment, the microfluidic device package may include the additional ports through which a sample may be supplied.

The microfluidic device initialization apparatus may be integrated with a sample analysis system of the microfluidic device 10. In an embodiment, the microfluidic device initialization apparatus may be set on a station of the sample analysis system. Using the sample analysis system including the microfluidic device initialization apparatus, a user may initialize the microfluidic device 10 on the sample analysis system before analyzing a sample, and may analyze the sample without moving the microfluidic device 10 to another apparatus. When the microfluidic device initialization apparatus is integrated with the sample analysis system, the above-described additional ports that supply a sample may be disposed on the lower and upper jigs 21 and 22 in addition to the first through third air pressure ports 29a, 29b and 29c.

Figure 7:
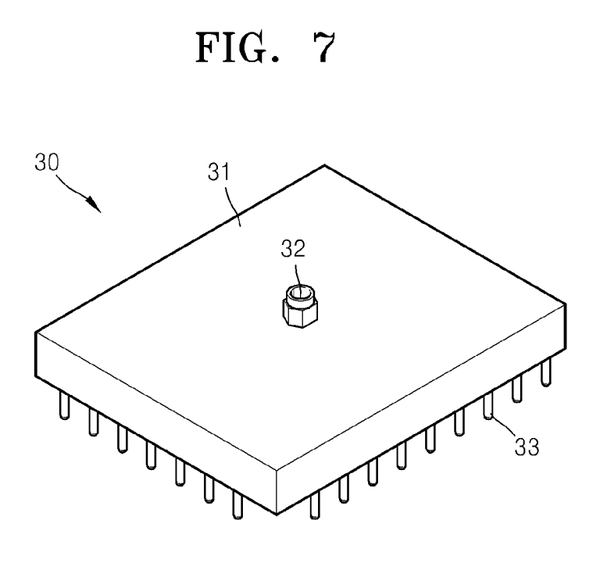
FIG. 7 is a perspective view of an embodiment of a multi-needle apparatus that initializes the microfluidic device shown in FIG. 1.

FIG. 7 is a perspective view of an embodiment of a multi-needle apparatus 30 that initializes the microfluidic device 10 illustrated in FIG. 1. FIG. 7 will now be described referring also to FIGS. 1 through 3.

As shown in FIG. 7, the multi-needle apparatus 30 may include a substrate 31, needles 33 disposed on a lower surface of the substrate 31, and an air pressure port 32 that may be connected to a vacuum pump or an air pressure pump to apply a negative pressure, e.g., a vacuum, and/or a positive pressure, e.g., an air pressure, to the microfluidic device 10 through the needles 33. As shown in FIG. 7, the air pressure port 32 is disposed on an upper surface of the substrate 31, but not being limited thereto. In another embodiment, the air pressure port 32 may be disposed on a side surface of the substrate 31. As shown in FIG. 7, one air pressure port 32 is disposed on the substrate 31, but not being limited thereto. In another embodiment, two or more air pressure ports 32 may be disposed on the substrate 31. The needles 33 may be disposed in an array corresponding to locations of the holes 15 formed in the microfluidic device 10. In an embodiment, the needles 33 may be disposed to correspond to the holes 15 related to opening and closing operations of the valves 17.

In another embodiment, two multi-needle apparatuses 30 may be formed in a pair to correspond to the holes 15 formed in the first substrate 11 of the microfluidic device 10 and the holes 15 formed in the second substrate 12 of the microfluidic device 10, respectively. More particularly, a multi-needle apparatus 30 including an array of the needles 33 corresponding to the holes 15 formed in the first substrate 11 of the microfluidic device 10 and a multi-needle apparatus 30 including an array of the needles 33 corresponding to the holes 15 formed in the second substrate 12 of the microfluidic device 10 may form a pair. When the needles 33 corresponding to the holes 15 formed in the first substrate 11 and to the holes 15 formed in the second substrate 12 are inserted into the holes 15, the microfluidic device 10 may be initialized as described in greater detail above with reference to FIGS. 4 and 5.

The general inventive concept should not be construed as being limited to the example embodiments set forth herein. Rather, the example embodiments are provided so that this disclosure will be thorough and complete and will fully convey the concept of the present invention to those of ordinary skill in the art.

In addition, while the general inventive concept has been particularly shown and described with reference to example embodiments thereof, it will be understood by those of ordinary skill in the art that various changes in form and details may be made therein without departing from the spirit or scope of the present invention as defined by the following claims.

What is claimed is:

1. A microfluidic device initialization apparatus comprising:
   a lower substrate;
   an upper substrate disposed opposite to the lower substrate;
   a lower fixing unit formed in an inner surface of the lower substrate;

an upper fixing unit formed in an inner surface of the upper substrate;

air pressure holes formed in each of the inner surface of the lower fixing unit in the lower substrate and the inner surface of the upper fixing unit in the upper substrate; and air pressure ports disposed on outer surfaces of the lower and upper substrates and wherein a negative pressure is supplied from an external device through portions of the air pressure ports while a positive pressure is supplied through other portions of the air pressure ports, wherein the lower substrate and the upper substrate are combined with each other at opposite sides of a microfluidic device to initialize the microfluidic device, the microfluidic device is disposed in a space defined by the lower and upper fixing units when the lower substrate and the upper substrate are combined with each other, and the negative pressure and the positive pressure are supplied to the microfluidic device through the respective air pressure holes.

2. The apparatus of claim 1, further comprising:

combination grooves formed in the inner surface of the lower substrate; and combination poles disposed on the inner surface of the upper substrate, wherein the combination poles are inserted into the combination grooves when the lower substrate and the upper substrate are combined with each other.

3. The apparatus of claim 1, wherein the air pressure holes formed in the lower fixing unit of the lower substrate are connected to holes formed in a first substrate of the microfluidic device when the microfluidic device is disposed between the combined upper and lower substrates.

4. The apparatus of claim 1, wherein the air pressure holes formed in the upper fixing unit of the upper substrate are connected to holes formed in a second substrate of the microfluidic device when the microfluidic device is disposed between the combined upper and lower substrates.

5. The apparatus of claim 1, wherein the air pressure holes formed in the lower and upper fixing units are connected to air inlet holes of the microfluidic device when the microfluidic device is disposed between the combined upper and lower substrates.

6. The apparatus of claim 1, wherein the air pressure ports comprise:

a first air pressure port disposed on the lower substrate; and second and third air pressure ports disposed on the upper substrate.

7. The apparatus of claim 6, wherein the first and second air pressure ports receive a positive pressure and the third air pressure port receives the negative pressure.

8. The apparatus of claim 6, wherein each of the first through third air pressure ports is one of an air pressure port through which at least one of the negative pressure and a positive pressure is supplied and a sample inlet port through which a sample is supplied.

9. The apparatus of claim 6, further comprising at least one sample inlet port disposed on the lower substrate and through which a sample is supplied.

10. The apparatus of claim 6, further comprising at least one sample inlet port disposed on the upper substrate and through which a sample is supplied.

11. The apparatus of claim 1, further including a sample analysis system which analyzes a sample using the microfluidic device.

12. A microfluidic device package comprising:

a microfluidic device comprising:

a first substrate:

a microfluidic channel disposed in the first substrate;

a valve seat disposed in the microfluidic channel and protruding from the first substrate;

a first hole formed in the first substrate and connected to the microfluidic channel;

a second substrate disposed opposite to the first substrate;

a space formed in the second substrate and corresponding to the valve seat;

a second hole formed in the second substrate and connected to the space; and a polymer film disposed between the first and second substrates; and a microfluidic device initialization apparatus comprising:

a lower substrate;

an upper substrate disposed opposite to the lower substrate;

a lower fixing unit formed in an inner surface of the lower substrate;

an upper fixing unit formed in an inner surface of the upper substrate;

air pressure holes formed in each of the inner surface of the lower fixing unit in the lower substrate and the inner surface of the upper fixing unit in the upper substrate; and air pressure ports disposed on outer surfaces of the lower and upper substrates and wherein a negative pressure is supplied from an external device through portions of the air pressure ports while a positive pressure is supplied through other portions of the air pressure ports, wherein the lower substrate and the upper substrate of the microfluidic device initialization apparatus are combined with each other at opposite sides of the microfluidic device, the microfluidic device is disposed in a space defined by the lower and upper fixing units, and is integrated between the lower and the upper substrates of the microfluidic device initialization apparatus, and the negative pressure and the positive pressure are supplied to the microfluidic device through at least one of the respective air pressure holes, the first hole and the second hole.

* * * * *